United States Patent
Bellingeri et al.

(10) Patent No.: US 12,354,733 B2
(45) Date of Patent: Jul. 8, 2025

(54) MANAGEMENT OF THE DISTRIBUTION OF GAS CYLINDERS IN A HOSPITAL FACILITY

(71) Applicant: L'Air Liquide, Société Anonyme pour l'Etude et l'Exploitation des Procédés Georges Claude, Paris (FR)

(72) Inventors: Federica Bellingeri, Paris (FR); Stephane Popovic, Gentilly (FR); Adrien Campagnac, Paris (FR); Adrien Mas, Paris (FR)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 562 days.

(21) Appl. No.: 17/672,408

(22) Filed: Feb. 15, 2022

(65) Prior Publication Data

US 2022/0262501 A1   Aug. 18, 2022

(30) Foreign Application Priority Data

Feb. 18, 2021  (FR) ........................................ 2101576

(51) Int. Cl.
*G06Q 10/087* (2023.01)
*G01F 23/18* (2006.01)
(Continued)

(52) U.S. Cl.
CPC ............ *G16H 40/20* (2018.01); *G01F 23/18* (2013.01); *G06Q 10/087* (2013.01); *H04Q 9/00* (2013.01); *H04Q 2209/40* (2013.01)

(58) Field of Classification Search
CPC ........ G16H 40/20; G16H 40/00; G01F 23/18; G06Q 10/087; G06Q 10/06; G06Q 50/22;
(Continued)

(56) References Cited

U.S. PATENT DOCUMENTS

| 7,552,731 B2 * | 6/2009 | Jorczak | A61M 16/0672 128/205.24 |
| 2004/0200477 A1 * | 10/2004 | Bleys | A61M 16/12 128/204.18 |

(Continued)

FOREIGN PATENT DOCUMENTS

| EP | 2848901 A1 * | 3/2015 | ............... G01F 1/86 |
| WO | WO-2015110724 A1 * | 7/2015 | ............ F17C 13/025 |

OTHER PUBLICATIONS

French Search Report for corresponding FR 2101576, Oct. 29, 2021.

*Primary Examiner* — Garcia Ade (74) *Attorney, Agent, or Firm* — Elwood L. Haynes (57) ABSTRACT

The invention relates to a method for managing mobile gas cylinders within a hospital facility (having care departments between which the gas cylinders travel and in which they are used. Each gas cylinder is equipped with a gas distribution valve with an electronic device for determining and supplying at least one item of gas amount information, and furthermore including a wireless communication module configured so as to transfer the gas amount information, via a wireless communication protocol, to data processing means, via a plurality of receivers, arranged in the care departments of the hospital facility. The data processing means process this gas amount information and drive a display on a display screen. An associated cylinder management installation.

14 Claims, 2 Drawing Sheets

(51) Int. Cl.
 *G16H 40/20* (2018.01)
 *H04Q 9/00* (2006.01)
(58) Field of Classification Search
 CPC ...... H04Q 9/00; H04Q 2209/40; F17C 13/02; F17C 13/04; F17C 2250/032; F17C 2250/0421; F17C 2250/0478
 USPC .......................................................... 705/28
 See application file for complete search history.

(56) References Cited

U.S. PATENT DOCUMENTS

| | | | |
|---|---|---|---|
| 2012/0130304 A1* | 5/2012 | Barish | A61M 13/003 604/24 |
| 2019/0107253 A1 | 4/2019 | Thind et al. | |
| 2019/0162617 A1 | 5/2019 | Quattrone | |
| 2020/0155268 A1* | 5/2020 | Beaudry | G16H 10/60 |

* cited by examiner

| | DEPARTMENT | ALLOCATION #DOT | STOCK #TOT | EMPTY TO REMOVE #V | FULL TO DELIVER #LIV |
|---|---|---|---|---|---|
| ⌄ | Pediatrics Building 1 2nd Floor | 12 | 9 | 9 | 10 |
| | Oxygen 2L | 4 | 4 | 4 | 4 |
| | Oxygen 5L | 4 | 4 | 3 | 3 |
| | Oxygen 11L | 4 | 1 | 2 | 3 |
| > | A&E 1 Building C Grd Floor | 7 | 5 | 3 | 5 |
| > | A&E 2 Building C Grd Floor | 5 | 5 | 3 | 3 |
| > | Trauma Building A 1st Floor | 7 | 8 | 4 | 3 |
| > | Surgery Building A 3rd Floor | 2 | 2 | 1 | 1 |
| Total | | 33 | 29 | 20 | 22 |

MANAGEMENT OF THE DISTRIBUTION OF GAS CYLINDERS IN A HOSPITAL FACILITY

CROSS REFERENCE TO RELATED APPLICATIONS

This application claims the benefit of priority under 35 U.S.C. § 119(a) and (b) to French Patent Application No. 2101576, filed Feb. 18, 2021, the entire contents of which are incorporated herein by reference.

BACKGROUND

The invention relates to a method for the improved management of the distribution of gas cylinders, in particular containing medicinal oxygen, that are able to be moved within a hospital facility, that is to say that are able to be transported from one location to another within this hospital facility, the medicinal oxygen being oxygen meeting the requirements of the Pharmacopoeia and meeting the requirements for marketing authorization.

Within a hospital facility, i.e. a hospital, clinic or the like, medicinal oxygen may be distributed by the network of gas pipelines in the building or be used in a form packaged into gas receptacles, commonly called gas cylinders, but also gas canisters or the like.

When medicinal oxygen is packaged into gas cylinders, it is mainly used to transfer patients undergoing oxygen therapy within hospital facilities, that is to say from one clinical department to another, or to carry out examinations in radiology of functional testing departments. Reference is then made to "mobile" gas cylinders, since they are able to be moved within hospital facilities between the time when they start being used and the time when they are returned, after being used, to the refilling centre of the gas supplier.

The caregiver has to balance two potentially contradictory objectives linked to "mobile" gas cylinders, specifically ensuring the safety of the patient being transferred by keeping the continuity of his oxygen therapy until he finishes being transferred and arrives in a department in which a new mobile oxygen cylinder will be available to replace the one that will have been emptied during the transfer and, moreover, ensuring effective use of mobile oxygen cylinders made available to him, including those that are partially emptied, so as to avoid wasting oxygen, and therefore controlling the cost of care provided to patients.

Specifically, depending on its capacity and/or the consumption of the oxygen that it contains, one and the same gas cylinder may be used multiple times, for example to perform successive transfers of multiple patients.

In other words, medical staff at the same time have to leave a minimum amount of residual oxygen in cylinders that have been used before returning the empty, or almost empty, cylinders to the conditioning centre of the gas supplier, in order to minimize losses and also avoid absolutely any interruption in the provision of oxygen to patients while they are being transferred or the like, and therefore make sure not to use a mobile gas cylinder not containing enough medicinal oxygen to guarantee a completely safe transfer of the patient.

This problem arises to a different extent from one care department to another, depending in particular on the criticality of the patients seen there, on the variety of their profile within one and the same care department, and on the duration of the transfers carried out from a given department, and therefore on the amount of oxygen consumed during each transfer.

The residual volume of oxygen below which a mobile oxygen cylinder is no longer able to be used to transfer a patient in complete safety will therefore vary from one department to another. By way of example, it will be higher in a resuscitation department caring for patients in a critical situation than in a general medical department that hospitalizes stable patients requiring smaller volumes of medicinal oxygen.

US-A-2019/0107253 proposes a method for tracking gas cylinders within a hospital, in which each gas cylinder is equipped with a gas distribution valve comprising an electronic device including a wireless communication module configured so as to transmit data, via a wireless communication protocol, to receiver beacons, arranged in hospital, which return said data to a data processing centre. The electronic device is equipped with a display screen that gives information relating to the gas cylinder on which it is installed.

However, this method does not make it possible to precisely manage the flows and the state of gas cylinders in the hospital. In particular, it does not make it possible to precisely ascertain the number of cylinders in each category, i.e. full, empty or partially empty, in each hospital department, and therefore does not make it possible to effectively manage the flows of cylinders in the hospital, in particular from one department to another, in particular so as to minimize gas losses and improve the restocking of gas, that is to say the flows of cylinders between the hospital and the one or more gas suppliers, i.e. the one or more conditioning centres.

Moreover, US-A-2019/0162617 proposes a method for calculating the remaining gas supply of a gas cylinder, in which a multifunction telephone (i.e. smartphone) or the like is used to capture an image of the dial of the manometer of a gas cylinder, which dial comprises a QR code marker or the like in front of which a rotating needle moves, the position of which needle with respect to the marker reflects the pressure in the cylinder under consideration. The image is processed by the telephone in order to deduce a remaining gas supply therefrom.

This method is tedious and does not make it possible to efficiently manage the flows and the state of gas cylinders in a hospital, since it requires the dial of the manometer of each cylinder to be photographed by the telephone. In addition, the screen of the telephone displays at best a remaining supply of the cylinder under consideration, but does not give any information relating to the whole fleet present at a given location. It is therefore not suitable for managing gas cylinders distributed between various care departments of a hospital facility.

One problem is thus that of being able to achieve effective and completely safe management of the fleet of gas cylinders, in particular those containing medicinal oxygen, distributed in the various care departments of a hospital facility, so as to be able to have, at all times, not only a state of the various cylinders located there (i.e. full, empty or partially empty, that is to say currently being used), but also their distribution by department, and preferably also by size or the like, specifically for the purpose of improving the flows of cylinders and restocking while minimizing gas losses.

SUMMARY

One solution of the invention then relates to a method, i.e. a process, for managing mobile gas cylinders within a hospital facility comprising multiple care departments between which gas cylinders travel and in which said gas cylinders are used, wherein:

a) each gas cylinder is equipped with a gas distribution valve comprising an electronic device configured so as to determine and supply at least one item of information about the amount of gas in the gas cylinder under consideration, and furthermore comprising a wireless communication module configured so as to transfer said at least one item of gas amount information, via a wireless communication protocol, and b) the hospital facility is equipped with a plurality of receivers arranged at least in the care departments and configured so as to receive said at least one item of gas amount information transmitted by gas cylinder present in said care departments and to transmit said at least one item of gas amount information to data processing means.

According to the method of the invention, the data processing means are configured so as to:

process said at least one item of gas amount information ($Q_g$) transmitted for each gas cylinder, and deduce therefrom whether each gas cylinder is at least a full gas cylinder or an empty gas cylinder and/or preferably a cylinder currently being used (i.e. partially empty), and command, on at least one display screen, a display, for one or more care departments, of at least:

the number of full gas cylinders (# P) present in the one or more care departments under consideration and the number of empty gas cylinders (# V) present in the one or more care departments under consideration, and preferably:

the number of gas cylinders currently being used (i.e. a cylinder that is no longer completely full and not yet empty, that is to say that has already started being used to supply gas) present in the one or more care departments under consideration and/or the total number of gas cylinders present in the one or more care departments under consideration.

Depending on the embodiment under consideration, the method of the invention may comprise one or more of the following features:

the data processing means are furthermore configured so as to command a display, for one or more care departments, of the number of gas cylinders currently being used and the total number of gas cylinders present in the one or more care departments under consideration.

the data processing means are configured so as to determine the total number of cylinders in at least one of the care departments under consideration, that is to say the stock of cylinders present, from the numbers of empty cylinders, full cylinders and cylinders currently being used.

the total number of cylinders corresponds to the sum of the numbers of empty cylinders, full cylinders and cylinders currently being used (i.e. neither totally empty nor totally full).

the data processing means are furthermore configured so as to command a display of a provision of cylinders for one or more of said care departments under consideration, that is to say the stock of cylinders allocated to said department.

each gas cylinder is identified by a specific cylinder identification (ID), that is to say a unique identifier specific to each gas cylinder.

the specific identification (ID) of each cylinder is stored within the electronic device fitted to the gas distribution valve.

the electronic device is configured so as to associate the gas amount information ($Q_g$) relating to a given gas cylinder with the identification (ID) of the gas cylinder under consideration, in particular a microprocessor arranged in said electronic device.

the identification (ID) of each cylinder is a serial number.

the gas amount information and the identification (ID) of the gas cylinder are transmitted together with one another.

the electronic device is configured so as to determine and supply at least one item of gas amount information ($Q_g$) chosen from a gas pressure or a volume of gas.

the wireless communication module is configured so as to transfer the gas amount information corresponding to each gas cylinder together with the identification (ID) of each gas cylinder under consideration.

each receiver, i.e. the receivers, is identified by a receiver identification ($ID_R$), that is to say unique and/or specific thereto.

the receivers are configured so as to transmit, to the data processing means, at least one item of gas amount information ($Q_g$) associated with a cylinder identification (ID) and with at least one identification of the receiver ($ID_R$) that received said at least one item of gas amount information ($Q_g$) associated with a cylinder identification (ID).

the specific receiver identification ($ID_R$) of each receiver is stored within the receiver under consideration.

the data processing means are configured so as to process said at least one item of gas amount information ($Q_g$) transmitted for each gas cylinder together with a cylinder identification (ID) and the identification of the receiver ($ID_R$) that received said at least one item of gas amount information ($Q_g$) so as to assign (i.e. associate) said at least one item of gas amount information ($Q_g$) associated with a cylinder identification (ID) to at least one care department of the hospital building corresponding to said receiver identification ($ID_R$).

the (i.e. each of the) receivers are configured so as to transmit datasets ($Q_g$, ID, $ID_R$) comprising an item of gas amount information ($Q_g$), a cylinder identification (ID) and an identification of the receiver ($ID_R$).

the data processing means are configured so as to process the datasets ($Q_g$, ID, $ID_R$) transmitted by the one or more receivers.

said at least one identification of the receiver ($ID_R$) is associated (i.e. paired) with and/or corresponds to at least one care department of the hospital building.

each association of the identification of a receiver ($ID_R$) with a care department, that is to say the correspondences between the receiver identifications ($ID_R$) and the care departments, is stored within storage means.

the data processing means are configured so as to go and retrieve the associations between identification of a receiver ($ID_R$) and corresponding care department that have been stored.

the gas amount information, the receiver identification ($ID_R$) and/or the identification (ID) of the gas cylinder are transmitted together in the form of a frame or computer code.

the frame or computer code comprises the identification (ID) of the cylinder under consideration, the gas amount information and the receiver identification

- ($ID_R$), and possibly one or more other additional items of information, in particular the datasets ($Q_g$, ID, $ID_R$).
- each care department comprises at least one receiver.
- the receivers form a network of receivers within the hospital building.
- the receivers are attached to the walls or to the ceilings of the care departments of the hospital facility.
- the receivers are supplied with electric power.
- the data processing means are arranged in the hospital facility or are located remotely from the hospital facility.
- the data processing means comprise one or more microprocessors.
- the data processing means comprise one (or more) computer(s) or computer server(s).
- the data processing means are configured so as to compare said at least one item of gas amount information ($Q_g$) transmitted for each gas cylinder present in one and the same care department with at least an upper threshold value (VS) and a lower threshold value (VSB) associated with the care department under consideration and to deduce therefrom whether each gas cylinder is:
  - a full gas cylinder when said at least one item of gas amount information ($Q_g$) is greater than or equal to said upper threshold value (VSH), i.e. $Q_g \geq VSH$, or
  - an empty gas cylinder when said at least one item of gas amount information ($Q_g$) is less than said lower threshold value (VSB), i.e. $Q_g < VSB$, where VSH>VSB, or
  - a gas cylinder currently being used when said at least one item of gas amount information ($Q_g$) is between the upper threshold value (VSH) and lower threshold value (VSB), i.e. $VSB < Q_g < VSH$.
- the upper threshold value (VSH) and lower threshold value (VSB) are gas pressure values (for example expressed in bar) or volume of gas values (for example expressed in litres).
- the upper threshold value (VSH) and lower threshold value (VSB) are stored by the electronic device.
- the upper threshold value (VSH) and lower threshold value (VSB) are configurable, that is to say may be adjusted or modified by the user, for example configurable by a care department, in particular so as to take into account specific features linked to various care departments.
- the upper threshold value (VSH) is greater than or equal to around 150 bar.
- the lower threshold value (VSH) is less than or equal to around 50 bar.
- the electronic device comprises storage means for storing/recording data, values or other information.
- the storage means comprise at least one computer memory, for example a flash memory or any other suitable memory.
- the data processing means are configured so as to determine the total number of gas cylinders present in each care department.
- the data processing means of the electronic device comprise one or more microprocessors, in particular a microcontroller.
- the data processing means of the electronic device comprise one or more microprocessors implementing one or more algorithms.
- the display screen is a computer screen, digital tablet screen or multifunction telephone screen.
- the care departments are chosen from among accident and emergency, traumatology departments, paediatric departments, surgical departments, intensive care departments or any other hospital department in which patients are cared for,
- the hospital facility is a hospital, a clinic or the like.
- the data processing means are furthermore configured so as to associate a given gas cylinder with a given care department, when the gas cylinder under consideration is detected by a (or the) receiver arranged in the care department under consideration, for a predefined duration (dt), that is to say after a time threshold able to be configured by the user, for example a duration of 0 to several tens of minutes, i.e. possibly reaching 1 to several hours. If the duration is set to 0, the gas cylinder under consideration is associated with a given care department, that is to say considered to form part thereof as soon as it is detected there, that is to say without any latency phase.
- the data processing means are configured so as to command the display, on said at least one display screen, for at least one care department, of at least the number of full gas cylinders and/or empty gas cylinders present in said at least one care department under consideration, and preferably the number of gas cylinders currently being used, that is to say that are neither full nor empty but contain an intermediate amount of gas, is also displayed,
- the gas cylinders are displayed in a manner distributed by size or capacity, and/or as a function of the gas that they contain.
- the cylinders contain a medical gas chosen from among oxygen or medicinal air, or a mixture of $NO/N_2$, $O_2/N_2O$, $He/O_2$, $Ar/O_2$, $Ar/N_2/O_2$, $Xe/O_2$ or any other medicinal gas.
- the cylinders preferably contain medicinal oxygen.
- the cylinders have internal volumes of between around 0.5 and 20 litres (equivalent in water).
- the electronic device comprises at least one sensor, in particular a pressure sensor.
- the electronic device comprises at least control means with a (at least one) microprocessor, and preferably the (one or more) microprocessor(s) is (are) carried by an electronic board.
- the wireless communication module is arranged in the electronic device.
- the electronic device is supplied with electric current by an electric current source in order to supply electric power to its components that require electric current to operate, in particular the one or more sensors, control means with a microprocessor, wireless communication module, etc.
- the electric current source comprises one (or more) preferably rechargeable battery (batteries) or cell(s).
- the cylinder comprises a protective cover arranged around the built-in regulator valve in order to protect it against impacts or other attacks, in particular a protective cover made of polymer, of metal or any other material.
- the electronic device is housed in an opening formed in the protective cover.
- the electric current source is arranged in a recess in the protective cover and connected electrically to the electronic device.
- the electronic device is joined to the built-in regulator valve, that is to say carried by the built-in regulator valve.
- the electronic device comprises an external housing containing all or some of its components.

the full gas cylinders are stored in the care departments before being used, the empty gas cylinders are stored, at least temporarily, in the care departments before being discharged.

the data processing means are furthermore configured so as to determine and command the display, on said at least one display screen, of the number of full gas cylinders to be supplied to a first care department and/or the number of gas cylinders of said first care department to be assigned to a second care department, on the basis of the number of empty and/or full cylinders, of the total number of cylinders and of the provision for said first and/or second care department.

BRIEF DESCRIPTION OF THE DRAWINGS

The invention will now be better understood from the following detailed description, which is given by way of a non-limiting illustration, with reference to the appended figures, in which.

DETAILED DESCRIPTION OF PREFERRED EMBODIMENTS

Figure 1:
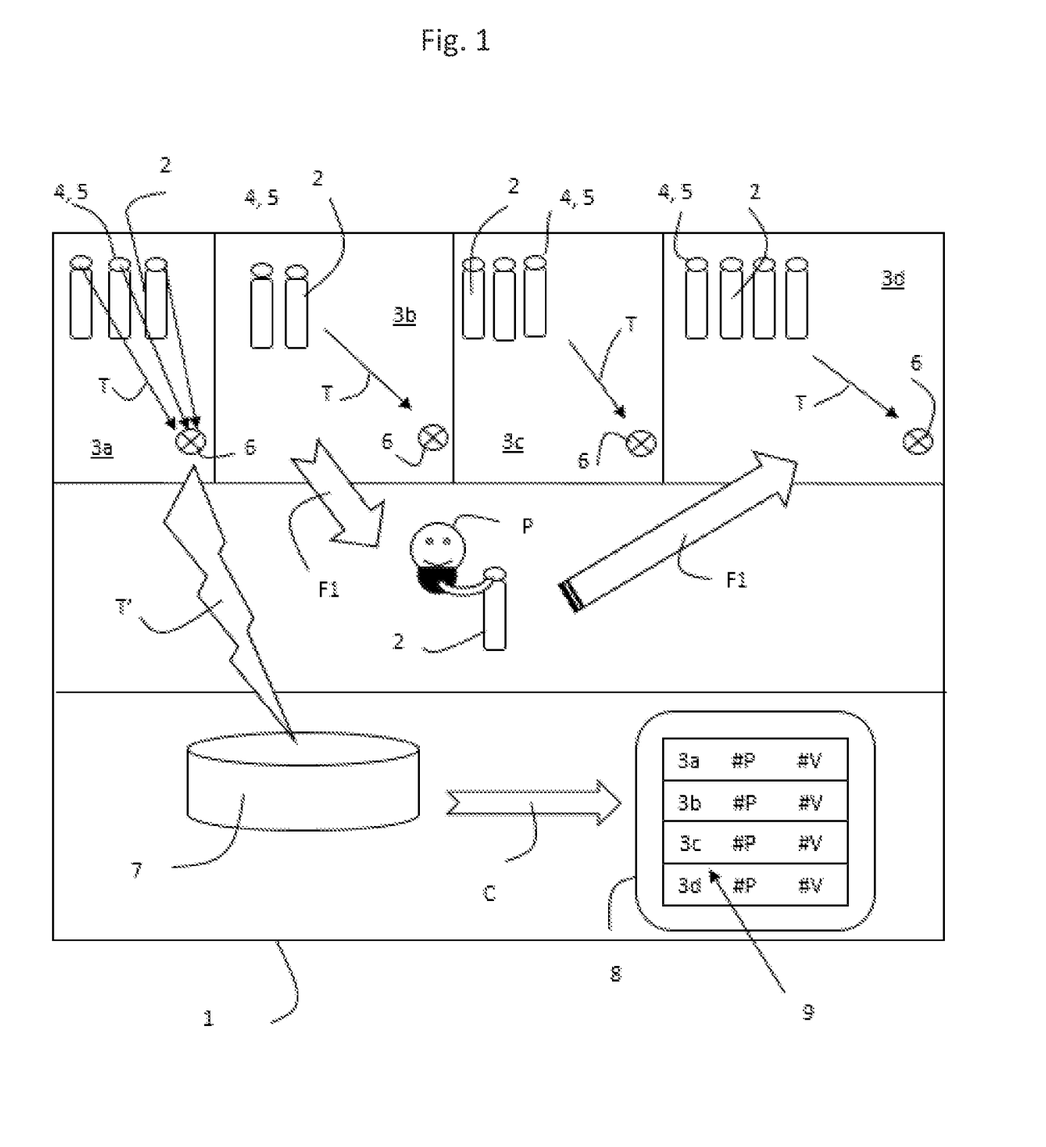
FIG. 1 schematically shows one embodiment of the method for managing mobile gas cylinders within a hospital facility according to the invention.

FIG. 1 schematically shows one embodiment of the method for managing gas cylinders 2, typically cylinders containing medicinal oxygen, able to move within a hospital facility 1, specifically a building in which patients are given hospital care, such as a hospital, a clinic or the like.

The hospital facility 1 comprises a plurality of care departments 3a-3d, for example a paediatric department, accident and emergency department, traumatology department, surgical department, etc. or the like, between which the gas cylinders 2 travel (arrows F1 and F2) while patients P are being transferred from one department to another. Each care department 3a-3d comprises one or more rooms or the like.

The gas cylinders 2 are therefore stored and/or used in the various care departments 3a-3d, or even during inter-department transfer phases.

FIG. 1 thus schematically shows the transfer (arrows F1 and F2), by a caregiver, for example a porter or a nurse, of a patient P supplied with oxygen by a medicinal oxygen cylinder 2, via a respiratory mask and a flexible tube, from a care department 3a to another care department 3d, for example from an accident and emergency department to a traumatology department.

Each gas cylinder 2, typically containing medicinal oxygen, is equipped with a gas distribution valve 4, preferably a built-in regulator valve, comprising an electronic device 5 and possibly a protective cover arranged around the gas distribution valve 4 and/or the electronic device 5 in order to protect them against impacts or the like.

The electronic device 5 is for example a gauge or a digital manometer for measuring and supplying information ($Q_g$) about the amount of gas in the gas cylinder 2 on which it is installed, typically the pressure or the residual volume of gas, for example by way of a pressure sensor.

The gas cylinders 2 are identified by a specific cylinder identification (ID). This cylinder identification (ID) is stored by the electronic device 5 fitted to the built-in regulator valve 4 fitted to each cylinder 2 The identification (ID) of each cylinder is preferably a serial number.

The gas amount information ($Q_g$) relating to a given gas cylinder, for example a pressure or a volume of gas, is associated with the identification (ID) of the gas cylinder under consideration so as to be able to ascertain the cylinder to which each item of captured gas amount information corresponds. This then gives a frame or a computer code that is able to be transmitted and that contains at least one gas cylinder identification (ID) associated with a determined amount of gas (i.e. pressure or volume) and optionally one or more other items of information.

The electronic device 5 also includes a wireless communication module configured so as to transfer (T) the gas amount information together with the cylinder identification (ID), via a wireless communication protocol, for example in Bluetooth mode, for example in Bluetooth Low Energy (BLE) mode, or any other suitable protocol, for example a UHF, infrared (IR), Lora or Sigfox protocol or the like. The wireless communication module comprises for example a microcontroller and a transmitter antenna.

A battery or the like supplies electric current to the electronic device 5 of each cylinder 2, in particular its internal components that require electric current to operate. The battery may be housed in a battery compartment in the protective cover protecting the built-in regulator valve 4 of each gas cylinder 2.

The electronic device 5 of each cylinder 2 communicates with receivers 6, that is to say beacons or the like, arranged at least in the various care departments 3a-3d of the hospital facility 1, that is to say in the various rooms, offices or locations in which the gas cylinders 2 are liable to be stored and/or used.

The receivers 6 typically comprise preferably wireless transceiver means for receiving information, i.e. measurements, data, signals or the like, transmitted by the electronic devices 5 fitted to the various cylinders 2 together with the ID of each cylinder, and for then transmitting (T') them to data processing means 7, preferably one (or more) microprocessor unit(s), such as a computer or a computer server that is remote or arranged in the hospital facility 1 or nearby.

More precisely, each receiver 6 is itself identified by a unique receiver identification $ID_R$, that is to say one specific thereto. This unique receiver identification $ID_R$ is stored by the receiver 6 under consideration. Each receiver identification ($ID_R$) in fact corresponds to a given care department in the hospital building.

When a receiver 6 receives an item of gas amount information ($Q_g$) associated with a cylinder ID, it then retransmits, to the data processing means, this gas amount information ($Q_g$) and this cylinder ID together with its own receiver identification ($ID_R$), that is to say datasets ($Q_g$, ID, $ID_R$).

For example, the gas amount information, the receiver identification ($ID_R$) and the identification (ID) of the gas cylinder, that is to say the datasets ($Q_g$, ID, $ID_R$), are transmitted together in the form of a frame or a computer code, which may furthermore possibly comprise one or more other additional items of information.

The receivers 6 are able to communicate with the data processing means 7 in Bluetooth mode or using an Internet or intranet network or the like, or via another protocol, such as Lora, Sigfox or a cellular network, for example.

In other words, the medicinal oxygen cylinders 2 are all equipped with an electronic device 5 such as a digital gauge or the like for ascertaining, at any time, the exact value of the pressure and the residual volume of oxygen in each medicinal oxygen cylinder 2, and also storing the ID of each cylinder on which it is mounted.

Provision is made, on each cylinder 2, for a wireless communication module, that is to say a communicating module, for transferring the gas amount information, in particular pressure and volume information, or even other information, together with the cylinder ID of the cylinder 2 under consideration using a wireless communication protocol, such that this information is then able to be captured by a network of receivers 6 carrying the data or information to data processing means 7, including in particular a centralized database.

Preferably, the wireless communication module is integrated into the electronic device 5 such as a digital gauge or the like fitted to each gas cylinder 2.

In addition, according to the invention, the data processing means 7 are configured so as to process the gas amount information ($Q_g$) transmitted for all of the gas cylinders 2 present in the various care departments 3a-3d of the hospital facility 1, which is associated with the ID of each of the cylinders and with the identification of a receiver ($ID_R$), therefore of a given care department, and then deduce therefrom whether each gas cylinder 2 is a full gas cylinder or an empty gas cylinder, or preferably also a cylinder currently being used, that is to say containing an intermediate amount of gas, and preferably also deduce therefrom the total number of cylinders 2 present in one or more care departments 3a-3d, preferably in each care department 3a-3d.

In particular, the data processing means are configured so as to process the gas amount information ($Q_g$) associated with the ID of each gas cylinder 2, and the identification ($ID_R$) of the receiver that received said gas amount information ($Q_g$) so as to assign or associate said gas amount information ($Q_g$) to or with a care department 3a-3d in the hospital building corresponding to the receiver identification ($ID_R$).

The correspondences between the identifications ($ID_R$) of the receivers 6 and the various care departments 3a-3d associated therewith are stored within storage means, such as a computer memory that is independent or contained directly in the data processing means 7. In any case, the data processing means 7 will go and retrieve the associations between identification of a receiver ($ID_R$) and corresponding care department 3a-3d that have been stored.

The data processing means 7 are furthermore configured so as to command, on one (or more) display screen(s) 8, a display 9, for the various care departments 3a-3d, of all or some of the numbers of cylinders 2 that have been determined, in particular the number of full gas cylinders 2 (# P) and/or the number of empty gas cylinders 2 (# V) and/or the number of cylinders currently being used and/or the total number of cylinders present in the one or more care departments 3a-3d under consideration.

Thus, a user, such as a caregiver, needing to use a gas cylinder 2 to transfer a patient from this care department 3a-3d to another care department 3a-3d, is able to ascertain immediately whether the gas cylinders 2 present in their current location are full gas cylinders 2 (# P), empty gas cylinders 2 (# V), or cylinders currently being used, and ascertain the number of cylinders in each category, which may also be displayed in a manner distributed by size when the cylinders are not all of the same size, for example 2 L, 5 L and 11 L cylinders (equivalent in water), or else distributed as a function of the type of gas that they contain, for example oxygen, air, etc.

All of this information is displayed on a display screen, as explained below.

By virtue of the invention, it is possible, in real time, to ascertain the total number of cylinders 2 present in each care department 3a-3d, and discriminate, depending on the wishes of the person needing this information, between full cylinders (# P), empty cylinders (# V), and/or cylinders currently being used, and even, if necessary, to obtain them classified by size or the like and/or by type of gas that they contain (i.e. $O_2$, air, etc.).

For this purpose, the data processing means 7 are configured so as to compare the gas amount information ($Q_g$) from all of the gas cylinders 2 contained in one and the same care department (3a-3d) with predefined threshold values (VS), in particular a lower threshold value (VSB) and an upper threshold value (VSH), where VSH>VSB, for example lower and upper reference pressures or lower and upper reference volumes, which threshold values are pre-recorded, i.e. stored by storage means, and preferably associated with the one or more care departments 3a-3d under consideration.

In other words, it is possible to define specific threshold values for each care department or else set identical threshold values for several or all departments.

The data processing means 7 then deduce, from these comparisons, whether the various gas cylinders 2 are full or empty gas cylinders, or else cylinders currently being used, that is to say cylinders that are no longer completely full since some of the gas has been used, but that are not yet empty.

A cylinder 2 is considered to be a full cylinder for the hospital department where it is located when the gas amount information ($Q_g$) for this cylinder 2 is greater than or equal to the pre-recorded upper threshold value (VSH) for the department in question, that is to say $Q_g \geq VSH$, for example a high pressure or a high volume.

By contrast, a cylinder 2 is considered to be an empty cylinder for the hospital department where it is located when the gas amount information ($Q_g$) for this cylinder 2 is less than a lower threshold value (VSB), i.e. $Q_g < VSB$, the lower threshold value (VSB) of course being much lower than the value of the upper threshold value (VSH).

For example, the upper pressure threshold value (VSH) may be set to 150 bar, or even to 180 bar, and the lower pressure threshold value (VSB) may be set to 50 bar, or even to 30 bar; or other values.

In the same way, expressed in litres, the upper threshold value (VSH) may for example be set to around 750 L and the lower threshold value (VSB) may for example be of the order of 250 L for a cylinder with a volume of 5 L (equivalent in water) that contains at most 1000 L of oxygen, that is to say, in this case, around 75% and 25% of the maximum volume, respectively. Of course, it is possible to choose other values for the two thresholds.

From there, a cylinder is considered to be currently in use when the gas amount information ($Q_g$) for this cylinder 2 is between the upper threshold value (VSH) and lower threshold value (VSB), this corresponding to a partially full cylinder.

By proceeding in this way, cylinder by cylinder 2 and department by department 3a-3d, the data processing means 7 are able to determine and count empty gas cylinders, full gas cylinders and gas cylinders currently being used that are present, at a given time, in the various care departments 3a-3d of the facility 1, and therefore also track their movements between these various care departments 3a-3d, resulting from transfers of patients P between departments.

In addition, knowing the empty gas cylinders, full gas cylinders and gas cylinders currently being used that are present, at a given time, in the various care departments 3a-3d of the facility 1 furthermore makes it possible to ascertain the total number of gas cylinders 2 present in the various departments at this given time.

An overall view of the situation may then be displayed 9 on one (or more) display screen(s) 8, for example the screen of a computer, of a touchscreen tablet or of a multifunction telephone (i.e. smartphone).

Each care department 3a-3d that has a display screen 8 may then be informed, in real time, about full cylinders 2, empty cylinders 2 and cylinders 2 currently being used that are located there. As already stated, the cylinders 2 may be displayed in a manner distributed by size and/or by type of gas that they contain.

It is also possible to display the provision of cylinders 2 for each department so as to be able to view and/or detect any surplus number or, by contrast, deficient number of cylinders 2 in one (or more) given department(s) and to be able to rectify this by adjusting the number of cylinders 2 that are located there, in particular when restocking, that is to say removing empty cylinders and replacing them with full cylinders.

All of this information may also be combined on one and the same screen that centralizes all cylinder tracking within the hospital facility. This greatly facilitates the overall management of the fleet of gas cylinders within the hospital or the like.

Preferably, each gas cylinder 2 is associated with the stock of the department 3a-3d in which it is located, that is to say all of the cylinders 2 that are located in this department, by virtue of being located by the receiver 6 present in this clinical department 3a-3d and carrying data to the data processing means 7, which processes said data in terms of computing.

In order to avoid a cylinder 2 assigned to the stock of a given clinical department changing assignment multiple times during the transfer of a patient P in the hospital, since the information transmitted by the cylinder 2 under consideration may be captured successively by the receivers 6 of the clinical departments 3a-3d passed through by the patient P during his inter-department transfer, the care department 3a-3d associated with a given cylinder 2 is modified only in the event of the cylinder 2 under consideration being detected by one and the same receiver 6 for a minimum duration defined by a time threshold able to be configured by the user, preferably a stored minimum duration. In some cases, this duration is zero (i.e. 0), that is to say that the cylinders 2 are immediately assigned to the stock of a department as soon as they are detected there. In other cases, they are assigned only after being present for several minutes, tens of minutes, or even one or more hours.

The information about the residual content of gas, for example of oxygen (i.e. residual pressure or volume), in each cylinder 2 is analysed by the data processing means 7 by being compared with one or more threshold values VS in order to determine whether each cylinder 2 is full, empty or currently being used (i.e. partially empty). Each threshold value may be defined differently for each care department 3a-3d in the hospital 1, so as to be adapted as best possible to the requirements and constraints of each care department 3a-3d.

In particular, "empty" cylinders 2 may thus be detected and identified for each department. However, when a cylinder 2 is considered to be "empty" in the department in which it is located but its content is greater than the lower threshold value VSB, that is to say the minimum value, defined for another less critical care department, the data processing means 7 are then configured so as to give the user a recommendation to transfer the cylinder 2 from the original department to the department in which its residual content will be able to be used to transfer a new patient in complete safety.

By contrast, when a cylinder 2 is considered to be "empty" for the department in which it is located, and no other department has a minimum threshold lower than its residual content, the data processing means 7 are configured so as to tell the user to replace this empty cylinder 2 with a full cylinder.

The user therefore has access to the information that a cylinder 2 is empty and should be replaced almost in real time, thereby making it possible to avoid any risk of a shortage of usable cylinders 2 in the care departments.

Figure 2:
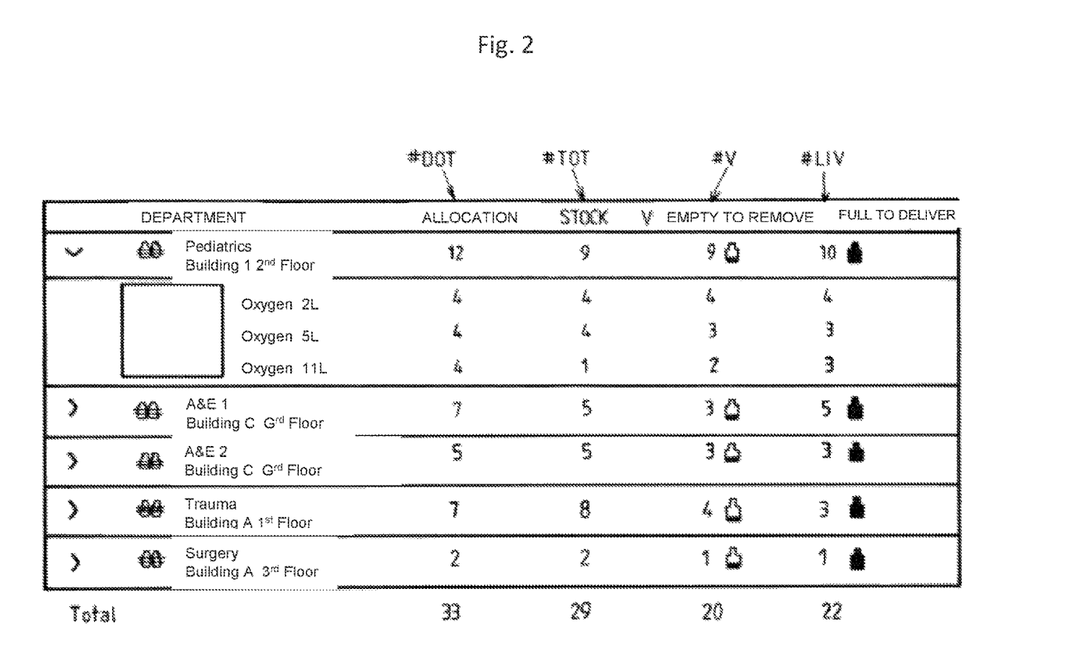
FIG. 2 schematically shows the display screen of a computer displaying the number of gas cylinders according to the method of the invention.

All of the information and recommendations are displayed in a manner distributed by care department and for example sizes of cylinders 2, as illustrated in FIG. 2.

FIG. 2 thus shows the display screen 8 of a computer or the like, on which the data processing means 7 command a display 9, for multiple care departments 3a-3d, of numbers of oxygen cylinders 2 that are located there, specifically here two accident and emergency departments and the traumatology, paediatric and surgical departments of the hospital.

More precisely, as may be seen, the total number of gas cylinders in stock (# TOT) and the number of empty gas cylinders (# V) that are located there are displayed for each of these departments.

Also displayed are the provision (# DOT) of cylinders for each department, that is to say the "target" number of cylinders assigned thereto, and the number of new cylinders to be supplied (# LIV) to each department given its provision, the stock located there and the number of empty cylinders in this stock.

The total number of gas cylinders in stock (# TOT) corresponds to the sum of the number of empty cylinders, full cylinders and cylinders currently being used. It should be noted that the number of full cylinders (# P) and/or cylinders currently used could also be displayed.

Moreover, as may be seen, for the paediatric department, the oxygen cylinders are displayed classified by size or capacity, specifically here 2 L, 5 L and 11 L oxygen cylinders, so as to precisely ascertain the number of cylinders in each category (i.e. size) that are present and/or need to be restocked (# LIV), as well as the number of empty cylinders (# V) that need to be removed and returned to the conditioning centre of the gas supplier in order to fill them with fresh gas. In this case too, it is also possible to display the number of full cylinders (# P) and/or cylinders currently being used by category.

Likewise, it is also possible to display the cylinders 2 present in all or some of these departments and that contain a gas other than oxygen, for example cylinders containing medicinal air or another medicinal gas.

All of this information makes it possible to ensure improved tracking and monitoring of the flows of cylinders in the hospital, department by department.

Thus, for the paediatric department, it will be understood that 9 empty cylinders need to be retrieved, i.e, removed, and returned to the gas supplier, comprising 4 2-L cylinders, 3 5-L cylinders and 2 11-L cylinders, and that 10 full cylinders need to be restocked so as to comply with the provision for this department, specifically 4 2-L cylinders, 3 5-L cylinders and 3 11-L cylinders.

Likewise, it may be seen that the traumatology department comprises an excess number of cylinders (i.e. 8 cylinders), that is to say greater than the provision for this department (i.e. 7 cylinders), Therefore, the 4 empty cylinders present in this department will be replaced with only 3 full cylinders in order, in this case too, to comply with the provision for this department.

In other words, by virtue of the invention, it is possible to easily take into account the difference between the target provision for a department and the real state of the stock of cylinders in this department and correct any potential difference by assigning this department the exact number of cylinders to which it is entitled, while still taking into account fluctuations in the number of cylinders within this department over time, in particular outward and return trips of patients in this department. This makes it possible to guarantee, over time, an effective assignment of the stock of cylinders in the hospital according to the requirements of each department.

In addition, this also makes it possible to achieve intelligent management of cylinders between the departments of the hospital, for example by transferring cylinders from one department to another in order to comply with the provisions for the departments in question, for example to organize a transfer from a department exceeding its provision due to a number of stored cylinders that are located there to another department in which the number of cylinders located there is insufficient, that is to say lower than its provision.

The transfer recommendations may also be given taking into account different empty cylinder thresholds (VSB). Thus, a first department, such as for example intensive care, may have a threshold VSB1 greater than the threshold VSB2 of a second, less critical department, for example paediatrics. In this case, a cylinder assigned to the first department and whose pressure is less than VSB1 is declared to be empty in this first department, but if its pressure is greater than VSB2, it may be transferred to the second department so as to continue to be used until it is considered to be empty in this second department.

Generally speaking, the invention thus also relates to an installation for managing mobile gas cylinders, configured so as to implement the method according to the invention, as described above, within a hospital facility comprising multiple care departments between which gas cylinders travel and in which said gas cylinders are used, comprising:
 data processing means with a microprocessor, such as a server,
 a plurality of receivers, arranged at least in the care departments of the hospital facility and configured so as to receive at least one item of gas amount information transmitted by the gas cylinders present in said care departments and to transmit said at least one item of gas amount information to the data processing means,
 at least one display screen, which is preferably present in the hospital facility,
and wherein:
 the data processing means are configured so as to:
  a) process said at least one item of gas amount information ($Q_g$) transmitted for each gas cylinder, and deduce therefrom whether each gas cylinder is a full gas cylinder, an empty gas cylinder or a cylinder currently being used, and
  b) command, on said at least one display screen, a display, for one or more care departments, of at least:
 the number of full gas cylinders (# P) present in the one or more care departments under consideration and
 the number of empty gas cylinders (# V) present in the one or more care departments under consideration,
and preferably:
 the number of gas cylinders currently being used present in the one or more care departments under consideration and/or
 the total number of gas cylinders present in the one or more care departments under consideration.

Such an installation is particularly well-suited to the management of mobile oxygen cylinders within hospital facilities.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for managing mobile gas cylinders within a hospital facility comprising multiple care departments between which gas cylinders travel and in which said gas cylinders are used, wherein:
 a. each gas cylinder is equipped with a gas distribution valve comprising an electronic device configured so as to determine and supply at least one item of information about the amount of gas in the gas cylinder under consideration, and furthermore comprising a wireless communication module configured so as to transfer said at least one item of gas amount information, via a wireless communication protocol, and
 b. the hospital facility is equipped with a plurality of receivers arranged at least in the care departments and configured so as to receive said at least one item of gas amount information transmitted by each gas cylinder present in said care departments and to transmit said at least one item of gas amount information to data processing means,
wherein the data processing means is:
 i. processing said at least one item of gas amount information transmitted for each gas cylinder, and deducing therefrom whether each gas cylinder is a full gas cylinder or an empty gas cylinder and/or possibly a cylinder currently being used, and
 ii. commanding, on at least one display screen, a display, for one or more care departments, of at least:
 the number of full gas cylinders present in the one or more care departments under consideration, and
 the number of empty gas cylinders present in the one or more care departments under consideration,
 and
 the number of gas cylinders currently being used present in the one or more care departments under consideration and/or
 the total number of gas cylinders present in the one or more care departments under consideration.

2. The method according to claim 1, wherein the electronic device is configured so as to determine and supply at least one item of gas amount information chosen from a gas pressure or a volume of gas.

3. The method according to claim 1, wherein the data processing means are configured so as to associate a given gas cylinder with a given care department, when the gas cylinder under consideration is detected by a receiver arranged in the care department under consideration.

4. The method according to claim 1, wherein each gas cylinder is identified by a specific cylinder identification stored by the electronic device and/or each receiver is identified by a receiver identification.

5. The method according to claim 4, wherein the electronic device is configured so as to associate the gas amount information relating to a given gas cylinder with the identification of the gas cylinder under consideration and with the identification of the receiver that received the gas amount information relating to the gas cylinder under consideration.

6. The method according to claim 4, wherein the wireless communication module is configured so as to transfer the gas amount information corresponding to each gas cylinder together with the identification of each gas cylinder under consideration and with the corresponding receiver identification.

7. The method according to claim 1, wherein the data processing means are configured so as to command the display, on said at least one display screen, for at least one care department, of the gas cylinders in a manner distributed by size or capacity and/or as a function of the gas that they contain.

8. The method according to claim 1, wherein the data processing means are furthermore configured so as to determine and command the display, on said at least one display screen:
   of the number of full gas cylinders to be supplied to a first care department, and/or
   of the number of gas cylinders in said first care department to be assigned to a second care department,
on the basis of the number of empty and/or full cylinders, of the total number of cylinders and of the provision for said first and/or second care departments.

9. The method according to claim 1, wherein the data processing means are configured so as to compare said at least one item of gas amount information transmitted for each gas cylinder present in one and the same care department with at least an upper threshold value and a lower threshold value associated with the care department under consideration and to deduce therefrom whether each gas cylinder is:
   a full gas cylinder when said at least one item of gas amount information is greater than or equal to said upper threshold value, or
   an empty gas cylinder when said at least one item of gas amount information is less than said lower threshold value, or
   a gas cylinder currently being used when said at least one item of gas amount information is between the upper threshold value and lower threshold value.

10. The method according to claim 9, wherein the upper threshold value and lower threshold value are stored by the data processing means and/or are configurable.

11. The method according to claim 4, wherein the data processing means are configured so as to retrieve the care department under consideration corresponding to the receiver identification.

12. The method according to claim 1, wherein the correspondences between the receiver identifications and the care departments are stored within storage means.

13. The method according to claim 9, wherein the upper threshold value is greater than or equal to 150 bar and the lower threshold value is less than or equal to 50 bar.

14. The method according to claim 9, wherein the cylinders contain a medical gas chosen from among oxygen or medicinal air or a mixture of $NO/N_2$, $O_2/N_2O$, $He/O_2$, $Ar/O_2$, $Ar/N_2/O_2$ or $Xe/O_2$.

* * * * *